(12) United States Patent
Webb

(10) Patent No.: US 7,264,630 B1
(45) Date of Patent: Sep. 4, 2007

(54) HOT/COLD THERAPY PACK

(76) Inventor: Nicholas J. Webb, 16314 Texas Springs Rd., Redding, CA (US) 96001

( * ) Notice: Subject to any disclaimer, the term of this patent is extended or adjusted under 35 U.S.C. 154(b) by 0 days.

(21) Appl. No.: 11/070,801

(22) Filed: Mar. 2, 2005

(51) Int. Cl.
*A61F 7/00* (2006.01)

(52) U.S. Cl. ............... 607/112; 128/898; 607/108; 607/114

(58) Field of Classification Search ............ 128/898; 607/108–114
See application file for complete search history.

(56) References Cited

U.S. PATENT DOCUMENTS

| | | | | |
|---|---|---|---|---|
| 2,635,175 | A * | 4/1953 | Hodge | 607/109 |
| 3,675,969 | A * | 7/1972 | Gage | 297/188.18 |
| 4,077,390 | A | 3/1978 | Stanley et al. | |
| 4,108,146 | A | 8/1978 | Golden | |
| 4,474,246 | A * | 10/1984 | Arroyo | 172/370 |
| 4,846,176 | A | 7/1989 | Golden | |
| 4,872,442 | A | 10/1989 | Manker | |
| 5,609,620 | A * | 3/1997 | Daily | 607/105 |
| 5,643,336 | A | 7/1997 | Lopez-Claros | |
| 5,897,581 | A * | 4/1999 | Fronda et al. | 607/109 |
| 5,956,763 | A * | 9/1999 | Blackshear | 2/49.1 |
| 6,126,683 | A * | 10/2000 | Momtaheni | 607/109 |
| 6,375,674 | B1 | 4/2002 | Carson | |
| 6,562,060 | B1 * | 5/2003 | Momtaheni | 607/109 |
| 6,669,715 | B2 | 12/2003 | Hoglund et al. | |
| 6,902,574 | B2 * | 6/2005 | Graham et al. | 607/111 |
| 2004/0010302 | A1 * | 1/2004 | von Hoffmann et al. | 607/114 |

* cited by examiner

*Primary Examiner*—Henry M Johnson, III
(74) *Attorney, Agent, or Firm*—Gordon & Jacobson, PC

(57) ABSTRACT

A thermal pack for applying thermal therapy to a human body part includes a flexible body that defines a cavity holding a thermal medium. A skeletal structure supports the flexible body. The skeletal structure is malleable such that it can be deformed around and held adjacent the human body part. The skeletal structure may be disposed within the cavity of the flexible body without being attached thereto and/or secured to an interior surface (and/or exterior surface) of the flexible body. The skeletal structure preferably includes a plurality of elongate leg portions that are wrapped around the human body part to hold the flexible body in place adjacent the treatment area during use. The thermal pack can be adapted for use with other mammalians.

29 Claims, 6 Drawing Sheets

HOT/COLD THERAPY PACK

BACKGROUND OF THE INVENTION

1. Field of the Invention

This invention relates broadly to heating and cooling mechanisms for treating a desired region of a patient's body. More particularly, this invention relates to heating and cooling therapy packs or pads that incorporate a liquid or gel substance that retains the desired thermal characteristics for application to the patient's body.

2. State of the Art

There are a variety of hot/cold therapy packs available on the market today. These products are available in many configurations. These variations include a textile component that accommodates a hot/cold pack comprised of a flexible plastic film and filled with water or gel that retains the desired thermal characteristics for an extended period of time (e.g., it retains a hot or cold temperature for an extended period of time after being heating or cooled). The textile component essentially provides a garment with straps that holds the hot/cold pack for the purpose of properly positioning the pack for extended periods of time during therapy treatment wherein the hot/cold temperature of the pack is applied to the patient's body locally in the vicinity of the pack.

Problematically, the textile components are often cumbersome and time-consuming to attach to the desired treatment area. Moreover, the textile components typically can be easily displaced during normal movement of the human body. Additionally, due to the varied structure of the human body between patients, the textile components fail to effectively provide a universal fit over a wide range of patients. Thus, the textile components are typically specialized with different shapes and sizes to accommodate the varied body structure between patients. This results in the need for retailers and users alike to maintain a wide inventory in order to accommodate both the combination of treatment sites and sizes. Furthermore, the straps of the textile component can often result in chafing and binding that can result in additional injury or the compromise of normal blood flow to the treatment area.

SUMMARY OF THE INVENTION

Therefore is the object of this invention to provide a single adult and/or a single child size hot/cold therapy pack that provides for the secure positioning of the hot/cold pack to the treatment site.

It is further the object of this invention to provide a product that can be used in first-aid stations or at home without the need for a variety of shapes and sizes to accommodate the wide range of human sizes and treatment sites.

It is also the object of this invention to provide an easy to use product that can be more rapidly positioned to a treatment site during a first aid emergency.

In the case of a child size configuration it is also an object of this invention to provide improved treatment compliance by incorporating a non-intimidating and child-friendly indicia (e.g., smiling face) on the body of the device structure.

It is a further object of this invention to provide a means of hot/cold therapy that significantly increases the attachment options so as to accommodate a wide range of human sizes and shapes.

In accord with these objects, which will be discussed in detail below, an improved thermal pack for applying thermal therapy to a human body part includes a flexible body that defines a cavity holding a thermal medium. A skeletal structure supports the flexible body. The skeletal structure is malleable such that it can be deformed around and held adjacent the human body part.

The skeletal structure may be disposed within the cavity of the flexible body without being attached to the walls of the flexible body. In such a configuration, the skeleton structure can float freely within the cavity. Alternatively, portions of the skeleton structure (e.g., its legs) can be tightly encapsulated by wall portions (e.g., leg portions) of the flexible body. In alternative embodiments, the skeletal structure can be secured to an interior surface or exterior surface of the flexible body.

Preferably, the skeletal structure includes a plurality of elongate legs that are wrapped around the human body part to hold the flexible body in place during use.

It will be appreciated that the thermal packs of the present invention are capable of providing both hot and cold therapy and easily conform to the desired treatment site for a wide range of human body parts and human body types. The thermal packs can readily be stored in a refrigerator for cold therapy by hanging it therein from one of its legs. They can also be hung underneath hot running water using one of its legs. The flexible and pliable structure of the legs provides for positioning over a wide range of human body parts and types and thus eliminates the need for multiple sizes. The thermal packs can readily be adapted for use with other mammalians, such as household pets and other domesticated animals.

According to one embodiment of the invention, the flexible body is realized by at least two thin flexible films that are affixed to one another about their periphery by adhesive, heat welding, encapsulation or other suitable means.

Additional objects and advantages of the invention will become apparent to those skilled in the art upon reference to the detailed description taken in conjunction with the provided figures.

DETAILED DESCRIPTION

Figure 1:
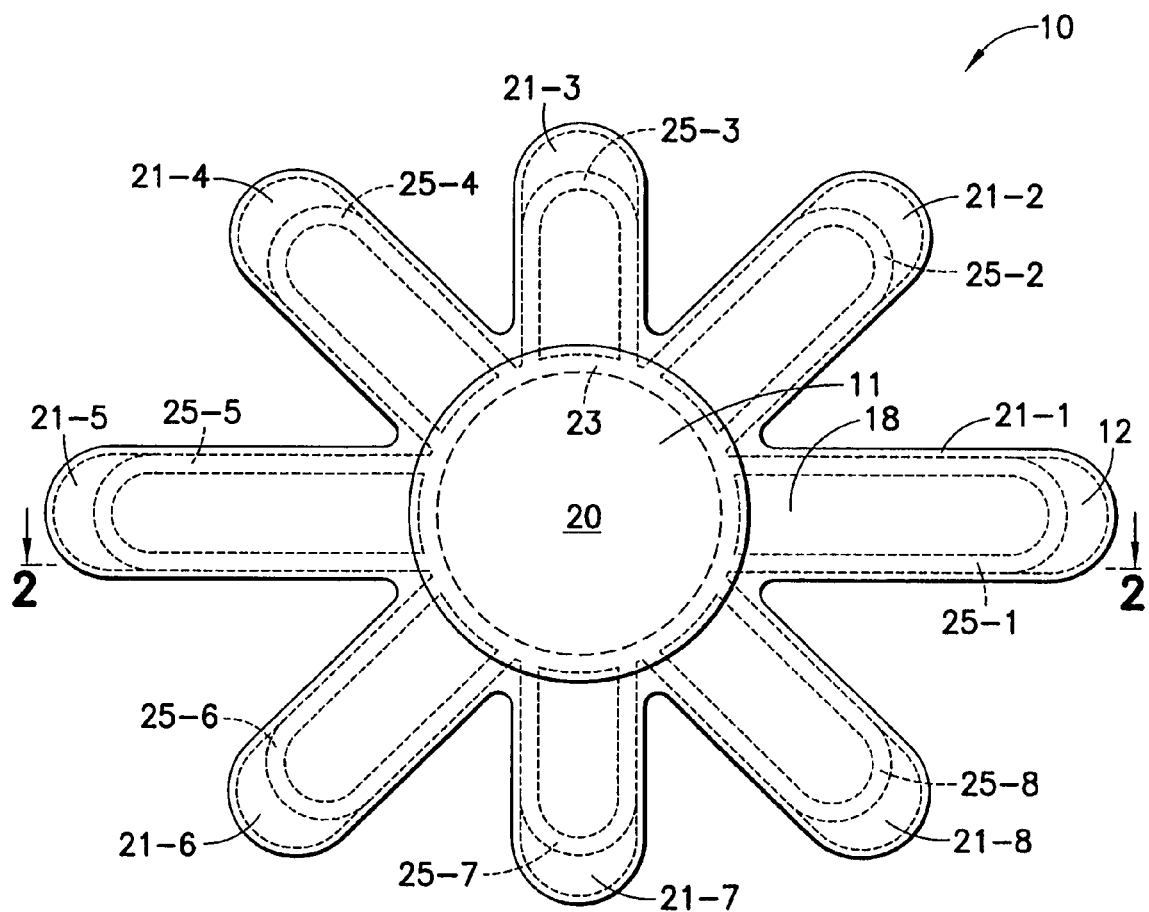
FIG. 1 is a top schematic view of an exemplary thermal pack in accordance with the present invention.
Figure 2A:
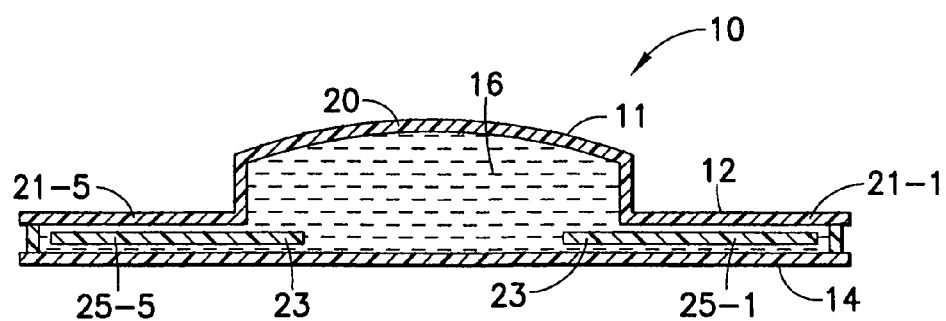
FIG. 2A is a cross-sectional view of a first embodiment of the thermal pack of FIG. 1.
Figure 2B:
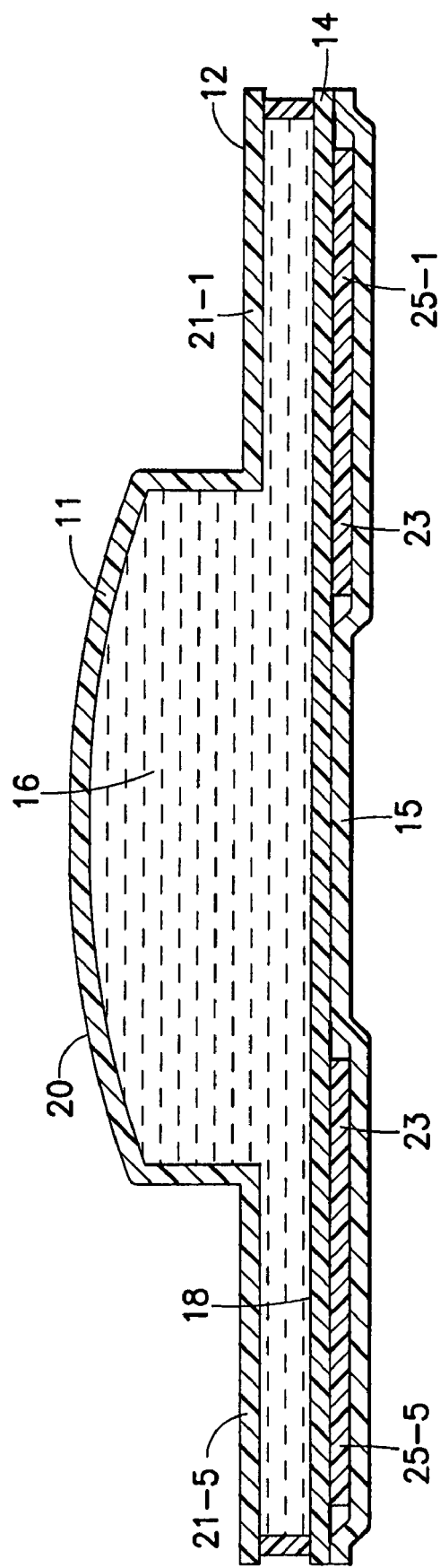
FIG. 2B is a cross-sectional view of a second embodiment of the thermal pack of FIG. 1.

Turning now to FIGS. 1, 2A and 2B, a thermal pack 10 in accordance with the present invention generally includes a flexible body 11 that is realized by an upper film 12 that is affixed to a lower film 14 about its periphery preferably by adhesive bonding, heat sealing, encapsulation or other suitable means. The upper and lower films 12, 14 are formed from a flexible and liquid impervious polymeric material. A chamber 16 is defined between the upper film 12 and lower
} film 14. The chamber 16 (or portions thereof) holds a thermal medium, such as a liquid or gel, that retains its thermal characteristics for an extended period of time after it has been heated or cooled. In the preferred embodiment, the thermal medium is realized by a gel that can be heated by exposure to hot water and that can be cooled in a refrigerator or freezer. Such gel typically employs clays or silicates, phase change material and chemicals to form aqueous colloidal dispersions. The phase change materials can be converted between solid and liquid phases and utilize their latent heat of fusion to cool or heat during such phase conversion. In another example, the gel may employ glycerine, distilled water, and starch as described in U.S. Pat. No. 6,554,787, herein incorporated by reference in its entirety. The thermal medium (and/or the upper film 12 and possibly the lower film 14) may be imparted with a color (for example, a purple, green, or blue color) in order to provide distinctiveness to the design.

A skeletal structure 18 supports the flexible body 11. The skeletal structure 18 is realized from a material that is malleable such that it generally retains its shape upon manual deformation, such as a stamped or die-cut flexible plastic material, a vinyl coated heavy wire (e.g., a vinyl coated aluminum wire) or other suitable material. In a first embodiment shown in FIG. 2A, the skeletal structure 18 is disposed within the chamber 16 without being attached to its walls. In such a configuration, the skeletal structure 18 can float freely within the chamber 16 where it is surrounded by the thermal medium. Alternatively, portions of the skeleton structure 18 (e.g., its legs) can be tightly encapsulated by wall portions (e.g., leg portions) of the chamber 16.

In a second embodiment shown in FIG. 2B, the skeletal structure 18 is secured to the bottom surface of the lower film 14 by a third flexible film 15 that encapsulates the skeletal structure 18. Such encapsulation is preferably accomplished by welding or bonding the third flexible film 15 to the bottom surface of the lower film 14 about the periphery (and possibly the central portion) of the body 11 as shown.

The flexible body 11 includes a central portion 20 (which preferably has a annular shape as best shown in FIG. 1) together with a plurality of elongate leg portions extending therefrom (for example, eight shown as 21-1 . . . 21-8). Preferably, the leg portions are equally spaced about the periphery of the central portion and can be classified into groups with different lengths. In the illustrative embodiment shown, the group 21-1 and 21-5 are longest, which is followed by the group 21-2, 21-4, 21-6, 21-8, which is followed by the group 21-3, 21-7. Similarly, the skeletal structure 18 includes a central ring portion 23 together with a plurality of elongate leg portions extending therefrom (e.g., eight leg portions 25-1 . . . 25-8) that support the corresponding leg portions 21-1 . . . 21-8 of the flexible body 11. In the first embodiment of FIG. 2A, the central ring portion 23 of the skeletal structure 18 is operably disposed between the central portion of the upper and lower films 12, 14 while the leg portions (25-1 . . . 25-8) of the skeletal structure 18 are operably disposed between the corresponding leg portions of the upper and lower films 12, 14. In the second embodiment of FIG. 2B, the central ring portion 23 of the skeletal structure 18 is secured to the central portion of the bottom surface of the lower film 14 while the leg portions (25-1 . . . 25-8) of the skeletal structure 18 are secured to the corresponding leg portions of the bottom surface of the lower film 14. In both configurations, the leg portions of the skeletal structure 18 are equally spaced about the periphery of its central portion and can be classified into groups with different lengths. In the illustrative embodiment shown, the group 25-1 and 25-5 are longest, which is followed by the group 25-2, 25-4, 25-6, 25-8, which is followed by the group 25-3 and 25-7.

Preferably, the upper film 12 is contoured such that the central portion 20 is elevated above the leg portions (e.g., leg portions 21-1 . . . 21-8) of the upper film 12 and thus defines a central reservoir between the central portion of the upper and lower films 12, 14. This central reservoir provides a large volume space to hold the thermal medium, which allows for increased duration of the hot or cold therapy carried by the thermal medium.

Figure 4:
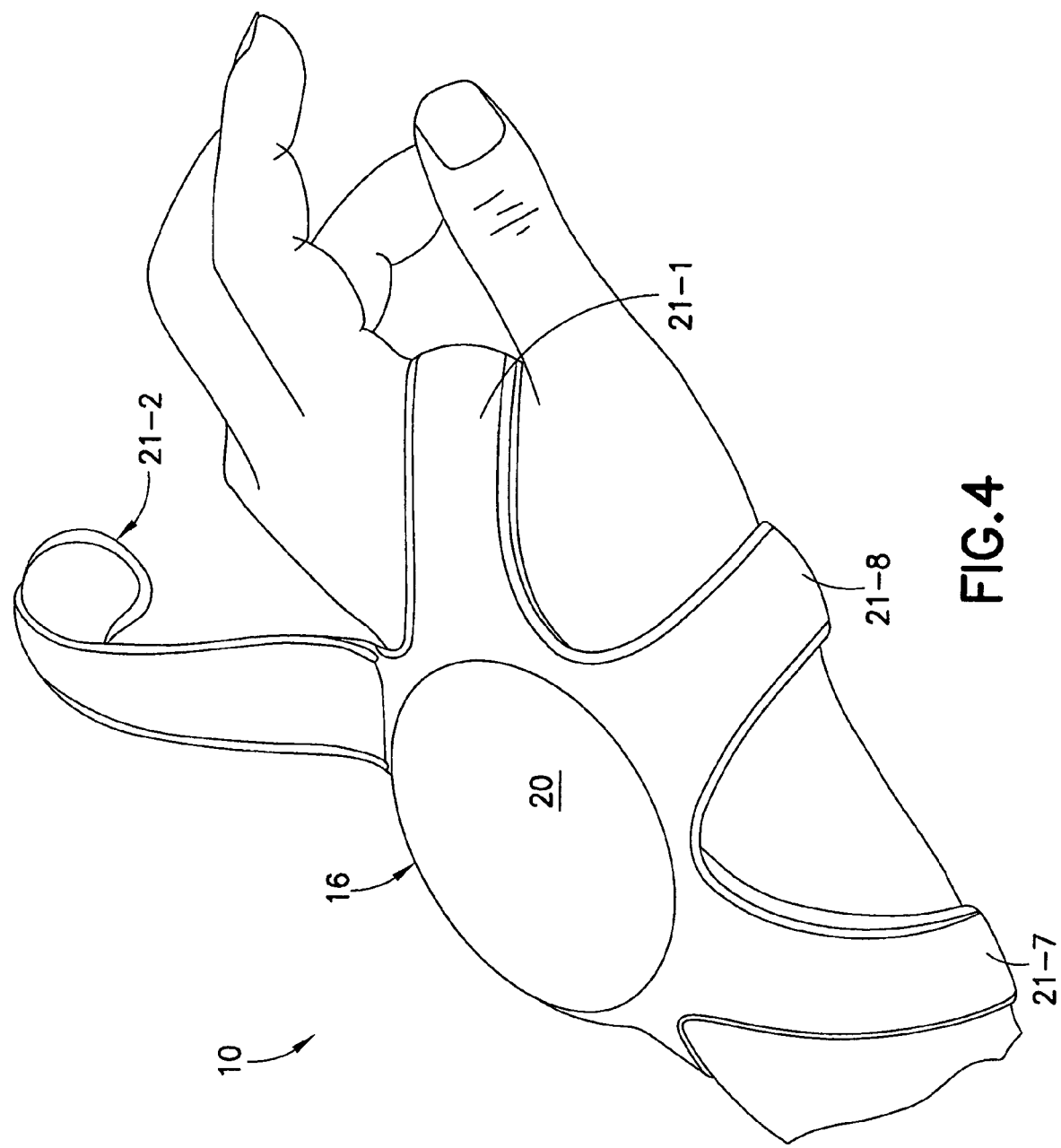
FIG. 4 is a pictorial illustration showing the thermal pack of FIG. 1 deformed around and secured to the top of a user's left wrist.

The leg portions 25-1 . . . 25-8 of the skeletal structure 18 are malleable such that they retain their shape upon deformation. During use, these leg portions are deformed around the human body part in the vicinity of the desired treatment area such that they support the thermal pack 10 adjacent the treatment area (FIG. 4). The deformation properties of the skeletal structure 18 cause the thermal pack 10 to retain its deformed shape and thus maintain the desired position adjacent the treatment area. In the preferred embodiment, the exterior surface which is operably disposed in contact with the treatment area (the bottom surface of the lower film 14 in FIG. 2A or the bottom surface of the third film 15 in FIG. 2B) is flocked or double-flocked or inlaid with a cloth fabric to thereby provide a soft and comfortable interface between the thermal pack 10 and the treatment area. Such an interface also provides minor insulation such that the hot or cold carried by the thermal medium does not directly contact the treatment area. Moreover, the upper film 12 is preferably transparent to allow the user to inspect the thermal medium held within the chamber 16.

Figure 3:
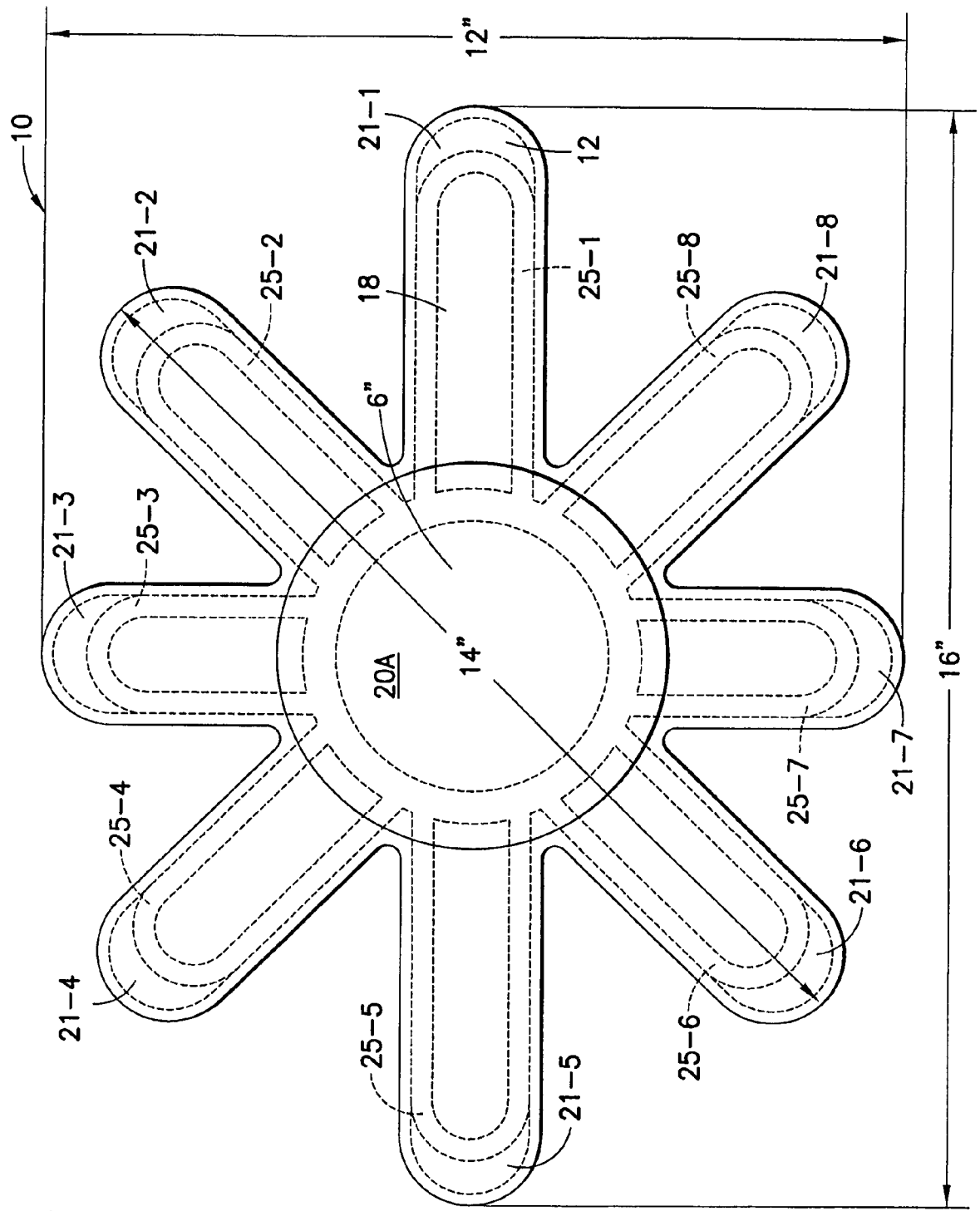
FIG. 3 a top schematic view of the thermal pack of FIG. 1 that shows exemplary dimensions intended for adult users.

As shown in FIG. 3, the central portion 20 of the flexible body 11 preferably has a circular shape with a diameter on the order of 6 inches. The leg portions 21-1, 21-5 extend from the central portion 20 at a length of approximately 5 inches such that the width spanning the opposing leg portion pairs is on the order of 16 inches. The leg portions 21-2, 21-4, 21-6, 21-8 extend from the central portion 20 at a length of approximately 4 inches such that the width spanning the opposing leg portion pairs is approximately 14 inches. The leg portions 21-3, 21-7 extend from the central portion 20 at a length of approximately 3 inches such that the width spanning the opposing leg portion pairs is approximately 12 inches. Similarly, the central ring portion 23 and the leg portions 25-1 . . . 25-8 of the skeletal structure 18 are sized to correspond to the leg portions of the flexible body 11 to which they support. Thus, the central ring portion 23 has a diameter slightly less than 6 inches. The leg portions 25-1 and 25-5 extend from the central ring portion 23 at a length of approximately 6 inches such that the width spanning the opposing leg portion pair is slightly less than 14 inches. The leg portions 25-2, 25-4, 25-6, 25-8 extend from the central ring portion 23 at a length of approximately 5 inches such that the width spanning the opposing leg portion pairs is slightly less than 12 inches. The leg portions 25-3 and 25-7 extend from the central ring portion 23 at a length of approximately 3 inches such that the width spanning the opposing leg portion pair is slightly less than 12 inches. Such dimensions are intended for adult users. The dimensions may be scaled down (for example, between 30 to 70% and preferably by 50%) such that the thermal pack is suitable for children. Moreover, it is contemplated that a graphical design (FIG. 5), such as a smiley face or other suitable visual indicia that is intended to be non-intimidating as well as interesting to child users of the device, may be printed or affixed to the exterior surface of the upper film 12 such that it is visible to the user during use. It is expected that such visual indicia will improve the willingness of the child user to use the device for its intended period of time and thus aid in usage compliance by child users.

In order to apply thermal therapy to a treatment area on the patient's body, the thermal pack 10 is heated or cooled such that the thermal medium held within the chamber 16 is heated or cooled to a desired temperature. In the preferred embodiment, the thermal pack 10 is heated by exposure to hot water and cooled in a refrigerator or freezer. It can supported from one of its legs and held under running hot water for heating. It can be hung from one of its leg inside a refrigerator or freezer for cooling. The hot/cold thermal pack 10 is then positioned such that the central portion 20 is adjacent the treatment area. While holding the thermal pack 10 in position over the treatment area, the thermal pack 10 is manually manipulated such that the skeletal structure 18 is deformed around the human body part in the vicinity of the treatment area (e.g., bent around the top of the wrist of the user as shown in FIG. 4 when treating such limb) such that it holds the thermal pack 10 adjacent the treatment area. The deformation properties of the skeletal structure 18 cause thermal pack 10 to retain its deformed shape and thus maintain the desired position adjacent the treatment area. With the thermal pack 10 properly positioned, the hot/cold carried by the thermal medium is effectively transferred to the treatment area. When the treatment is to be terminated, the skeletal structure 18 is bent to free-up the body part such that the thermal pack 10 can readily be separated therefrom. This process can be repeated over the same treatment site to provide for thermal therapy over a longer period of time. Alternatively, this process can be repeated such that the pack is positioned over a different treatment site and different human body part in order to apply thermal therapy thereto. Advantageously, the adaptable structure of the legs provides for flexible positioning over a wide range of human body parts and types and thus eliminates the need for a large number of shapes and sizes.

Figure 5:
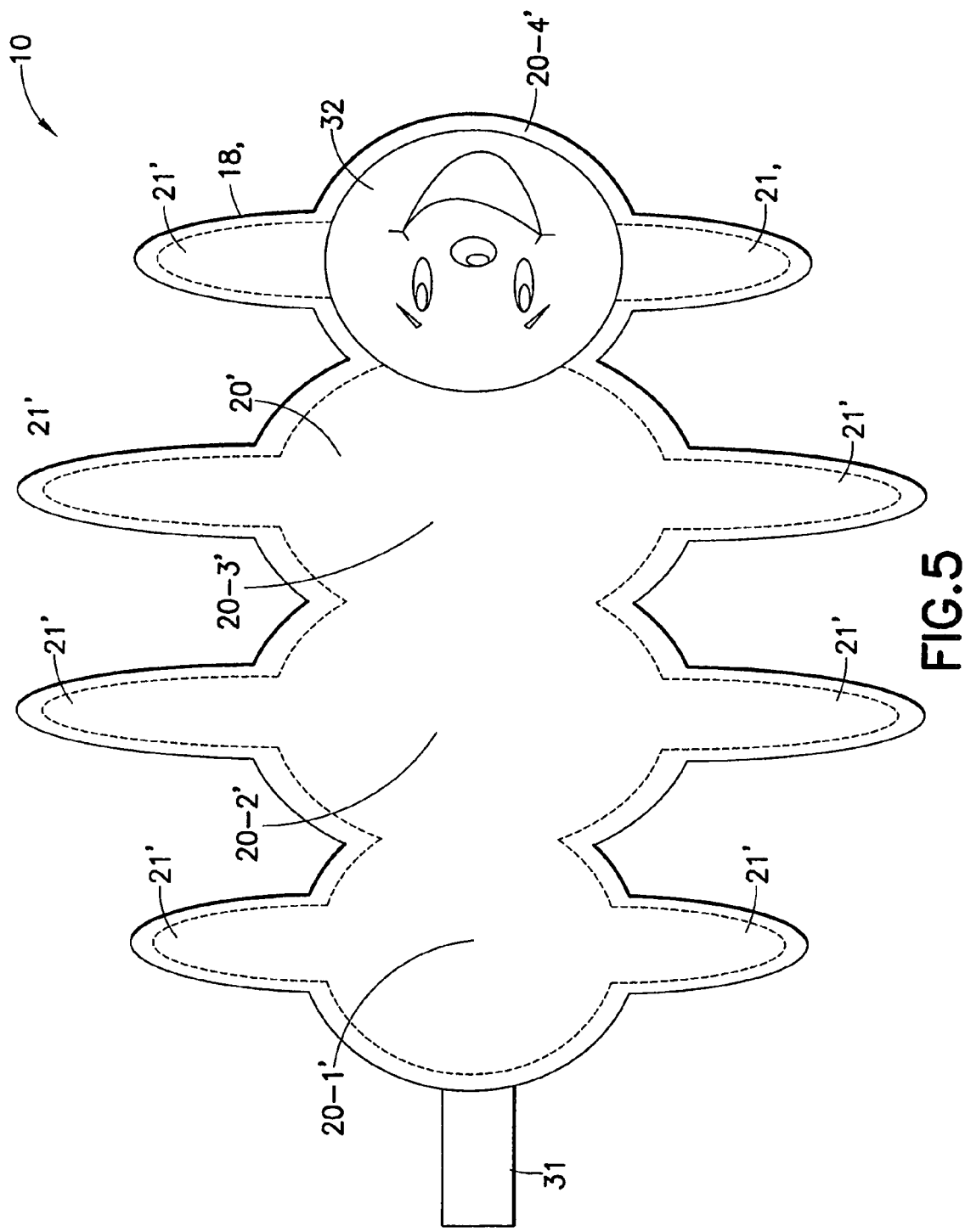
FIG. 5 is a top schematic view of an alternate thermal pack in accordance with the present invention.

In alternative embodiments, the shape and profile of the thermal pack 10 may be modified for different applications. For example, as shown in FIG. 5, a thermal pack 10' is shown with an elongate multi-segment central portion 20' and legs 21' that are all defined by the upper and lower films and a skeletal structure 18' therebetween. The elongate multi-segment central portion 20' (which preferably has four generally elliptical shaped segments 20-1', 20-2', 20-3', 204' as shown) defines a central reservoir between the upper and lower films similar to the central portion 20 of FIGS. 1, 2A, 2B. This central reservoir provides a large volume space to hold the thermal medium. The legs 21' extend from opposite sides of the segments of the central portion 20' at directions substantially orthogonal to the longitudinal axis of the elongate central portion 20' as shown. A warning label 31 is preferably affixed to an end of the elongate multi-segment central portion 20' as shown.

Figure 6:
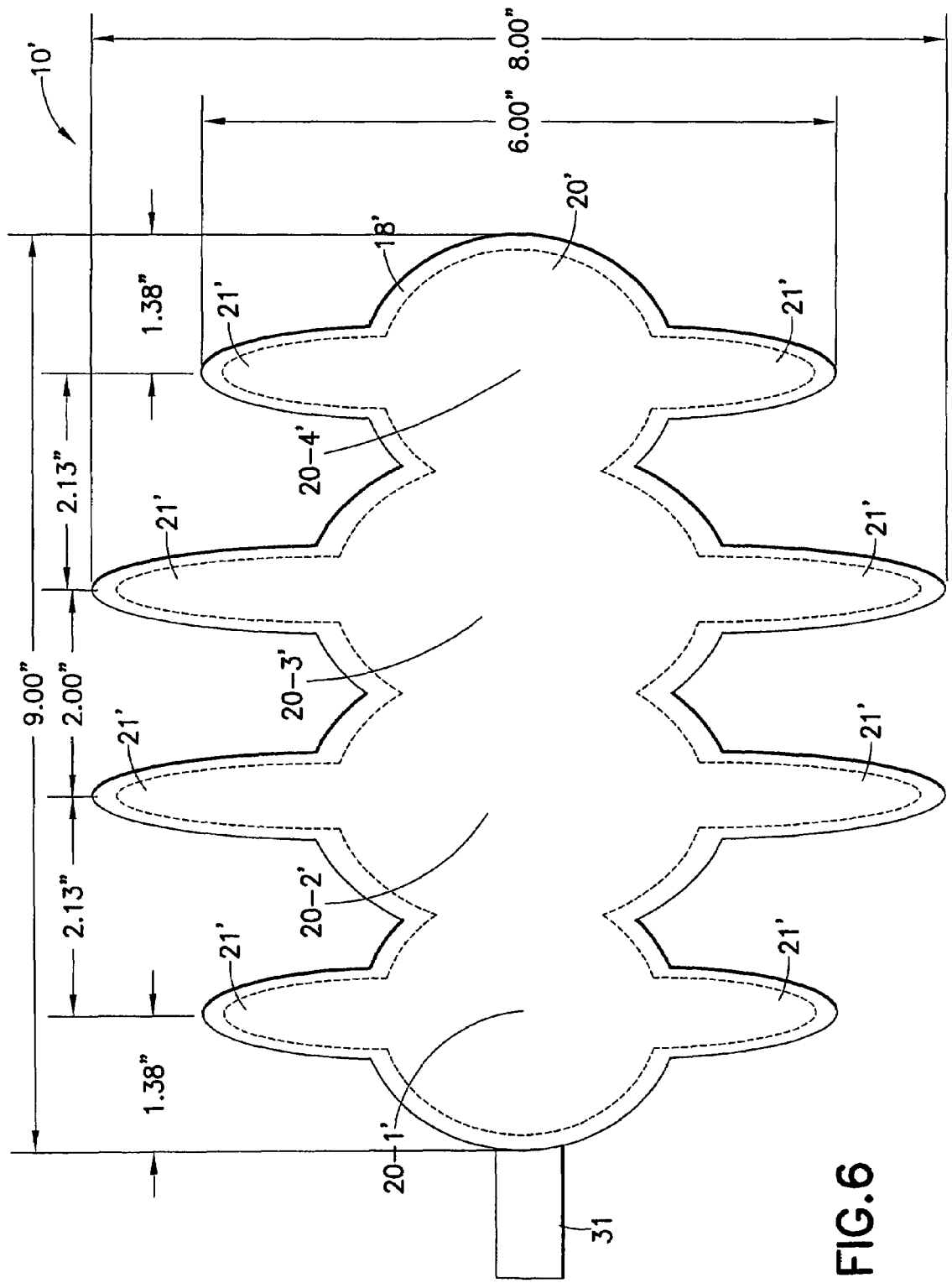
FIG. 6 a top schematic view of the thermal pack of FIG. 5 that shows exemplary dimensions intended for adult users.

As shown in FIG. 6, the elongate multi-segment central portion 20' is preferably on the order of 9 inches long with a set of longer legs that extend from the middle segments to a width spanning these legs on the order of 8 inches and a set of shorter legs that extend from the end segments to a width spanning these legs on the order of 6 inches. The short legs are spaced on the order of 1.38 inches from the end of thermal pack 10' along its lengthwise direction, the long legs are spaced on the order of 2.13 inches from the short legs along the lengthwise direction, and the long legs are spaced on the order of 2.00 inches from one another along the lengthwise direction as shown. Such dimensions are intended for adult users and by way of a preferred example only. The dimensions may be scaled down (for example, between 30-70% and preferably 50%) such that the thermal pack is suitable for children. Moreover, it is contemplated that a child-friendly graphical design 32 (or possibly other visual indicia) may be printed or affixed to the upper surface of the elongate central portion 20' such that it is visible to the user as described above.

In yet other alternative embodiments, the skeletal structure 18 may be attached (for example, by an adhesive bond, thermal welding and/or encapsulation) to an interior and/or an exterior surface of the body (e.g., the upper film 12 and the lower film 14 of FIG. 2A) that holds the thermal medium. In such configurations, the legs of the body may be omitted such that the legs of the skeletal structure extend alone from a body that holds the thermal medium.

Advantageously, the thermal packs of the present invention are capable of providing both hot and cold therapy and easily conform to the desired treatment site for a wide range of body types. The thermal packs can readily be stored in a refrigerator for cold therapy by hanging it therein from one of its legs. They can also hung underneath hot running water using one of its legs. The adaptable structure of the elongate legs provides for flexible positioning over a wide range of body parts and body types and thus eliminates the need for a large number of shapes and sizes. Moreover, the legs grab and conform to the treated body part at multiple points, which minimizes the local pressure applied to the treated body part and helps prevent any adverse impact to blood circulation through the treated body part that may be caused by increased local pressure to the body part.

There have been described and illustrated herein several embodiments of a repositionable thermal pack and corresponding method of operation. While particular embodiments of the invention have been described, it is not intended that the invention be limited thereto, as it is intended that the invention be as broad in scope as the art will allow and that the specification be read likewise. Thus, while particular shapes, profiles and configurations of the inner and outer walls of a bag that holds the thermal medium have been disclosed, it will be appreciated that other shapes, profiles and configurations can be used as well. In addition, while particular shapes, configurations and types of skeletal structures have been disclosed, it will be understood other shapes, configuration and types of deformable and pliable structures can be used. For example, and not by way of limitation, the skeletal structure might possibly employ a solid stamped or die-cut structure or an inverted christmas-tree like structure for each one of its legs. In another example, the flexible body that holds the thermal medium may have an elongate (e.g., tubular) shape that it supported by an elongate (e.g., tubular) malleable skeletal structure. During use, the elongate flexible body and skeletal structure are wrapped around the desired human body part and the deformation properties of the skeleton structure holds the flexible body in place about the human body part to allow the hot/cold carried by the thermal medium to transfer to the desired human body part. The thermal packs can readily be adapted for use with other mammalians, such as household pets and other domesticated animals. It will therefore be appreciated by those skilled in the art that yet other modifications could be made to the provided invention without deviating from its spirit and scope as claimed.

What is claimed is:

1. An apparatus for applying thermal therapy to a mammalian body part, the apparatus comprising:

a flexible body that defines a cavity holding a thermal medium; and a skeletal structure, distinct from said flexible body, adapted to support said flexible body, said skeletal structure being malleable such that it can be deformed around the body part such that said flexible body is held adjacent the mammalian body part, wherein said skeletal structure is disposed within the cavity of the flexible body without being attached to said flexible body.

2. An apparatus according to claim 1, wherein:
said skeletal structure includes a central portion and plurality of narrow leg portions that extend from said central portion.

3. An apparatus according to claim 2, wherein:
said central portion comprises an annular shaped ring.

4. An apparatus according claim 2, wherein:
said central portion comprises an elongate multi-segment structure.

5. An apparatus according to claim 2, wherein:
said flexible body comprises a central portion corresponding to said central portion of said skeletal structure.

6. An apparatus according to claim 5, wherein:
said central portion of said flexible body defines a portion of said cavity that contains said central portion of said skeletal structure.

7. An apparatus according to claim 6, wherein:
said flexible body comprises a plurality of narrow leg portions corresponding to said narrow leg portions of said skeletal structure.

8. An apparatus according to claim 7, wherein:
a portion of said cavity defined by said narrow leg portions of said flexible body contains said narrow leg portions of said skeletal structure.

9. An apparatus according to claim 2, wherein:
said central portion has a maximum dimension of at least 3 inches.

10. An apparatus according to claim 9, wherein:
said central portion has a maximum dimension of at least 6 inches.

11. An apparatus according to claim 2, wherein:
pairs of said leg portions extend from said central portion in opposite directions.

12. An apparatus according to claim 11, wherein:
a width spanning a given pair of leg portions is at least 5 inches.

13. An apparatus according to claim 11, wherein:
said pairs include a first set of leg portion pairs that are shorter than a second set of leg portion pairs.

14. An apparatus according to claim 13, wherein:
a first width spanning a given pair belonging to said fist set of leg portion pairs is at least 5 inches, and a second width spanning a given pair belonging to said second set of leg portion pairs is at least 6 inches.

15. An apparatus according to claim 1, wherein:
said skeletal structure comprises one of a deformable metal structure and a deformable plastic structure.

16. An apparatus according to claim 15, wherein:
said deformable metal structure comprises a vinyl coated metal wire.

17. An apparatus according to claim 15, wherein:
said deformable plastic structure comprises a stamped or die-cut deformable plastic structure.

18. An apparatus according to claim 1, wherein:
said flexible body includes a soft surface for contacting the mammalian body part.

19. An apparatus according to claim 1, wherein:
said flexible body comprises visual indicia printed thereon, said visual indicia intended to be non-intimidating as well as interesting to child users of said apparatus.

20. An apparatus according to claim 1, wherein:
the flexible body is realized by at least two thin flexible films that are affixed to one another.

21. A method of applying thermal therapy to a mammalian body part, the method comprising:
  i) providing an apparatus including
    a flexible body that defines a cavity holding a thermal medium, and
    a skeletal structure adapted to support said flexible body, said skeletal structure being flexible and malleable;
  ii) manipulating said skeletal structure such that it is deformed around the body part and holds said flexible body adjacent the body part, thereby applying thermal therapy to the mammalian body part; and
  iii) heating or cooling the thermal medium, wherein the heating is accomplished by exposing the thermal medium to hot water, and/or the cooling is accomplished by exposing the thermal medium to cold temperatures in a refrigerator or freezer.

22. An apparatus for applying thermal therapy to a mammalian body part, the apparatus comprising:
a flexible body that defines a cavity holding a thermal medium; and
a skeletal structure comprising a plurality of elongate leg members that are adapted to support said flexible body, said skeletal structure being malleable such that a portion of said plurality of elongate leg members can be deformed around the mammalian body part such that said flexible body is held adjacent the mammalian body part.

23. An apparatus according to claim 22, wherein:
said skeletal structure is disposed within the cavity of the flexible body without being attached to said flexible body.

24. An apparatus according to claim 22, wherein:
said flexible body has at least one interior surface, and said skeletal structure is secured to said at least one interior surface of said flexible body.

25. An apparatus according to claim 24, wherein:
said flexible body includes two films that define said cavity therebetween, and a third film that encapsulates said skeletal structure against one of said two films.

26. An apparatus according to claim 22, wherein:
said flexible body has at least one exterior surface, and said skeletal structure is attached to said at least one exterior surface of said flexible body.

27. An apparatus according to claim 22, wherein:
said skeletal structure comprises one of a deformable metal structure and a deformable plastic structure.

28. An apparatus according to claim 27, wherein:
said deformable metal structure comprises a vinyl coated metal wire.

29. An apparatus according to claim 27, wherein:
said deformable plastic structure comprises a stamped or die-cut deformable plastic structure.

* * * * *